(12) United States Patent
Baru et al.

(10) Patent No.: US 9,895,542 B2
(45) Date of Patent: Feb. 20, 2018

(54) DEVICE AND METHOD FOR SELECTIVE NERVE STIMULATION

(71) Applicant: BIOTRONIK SE & Co. KG, Berlin (DE)

(72) Inventors: Marcelo Baru, Tualatin, OR (US); Andrew B. Kibler, Lake Oswego, OR (US)

(73) Assignee: BIOTRONIK SE & Co. KG (DE)

( * ) Notice: Subject to any disclaimer, the term of this patent is extended or adjusted under 35 U.S.C. 154(b) by 0 days.

(21) Appl. No.: 15/090,690

(22) Filed: Apr. 5, 2016

(65) Prior Publication Data

US 2016/0310741 A1    Oct. 27, 2016

Related U.S. Application Data

(60) Provisional application No. 62/150,865, filed on Apr. 22, 2015.

(51) Int. Cl.
*A61N 1/36* (2006.01)
*A61N 1/05* (2006.01)

(52) U.S. Cl.
CPC ........ *A61N 1/36114* (2013.01); *A61N 1/0556* (2013.01); *A61N 1/36053* (2013.01); *A61N 1/36185* (2013.01)

(58) Field of Classification Search
CPC .............. A61N 1/3605; A61N 1/36053; A61N 1/36057; A61N 1/36114; A61N 1/36178
USPC .............................................. 607/70, 72, 74
See application file for complete search history.

(56) References Cited

U.S. PATENT DOCUMENTS

| | | | |
|---|---|---|---|
| 4,703,192 A | * | 10/1987 | Ferguson ................ H02J 9/062 307/64 |
| 5,199,430 A | | 4/1993 | Fang et al. |
| 7,389,145 B2 | | 6/2008 | Kilgore et al. |
| 8,615,294 B2 | | 12/2013 | Ben-David et al. |
| 2003/0212440 A1 | | 11/2003 | Boveja |
| 2004/0162594 A1 | | 8/2004 | King |

(Continued)

FOREIGN PATENT DOCUMENTS

EP         1 392 393 A1    3/2004
WO    WO 2007/012907 A2    2/2007

OTHER PUBLICATIONS

European Search Report, Appln. No. 16164037.0-1666, Sep. 16, 2016.

(Continued)

*Primary Examiner* — Allen Porter, Jr.
(74) *Attorney, Agent, or Firm* — Craig A. Fieschko, Esq.; DeWitt Ross & Stevens S.C.

(57) ABSTRACT

An implantable pulse generator (106) provides electric stimulation pulses for nerve stimulation via a stimulation lead (100) having stimulation electrodes (102, 104). The electric stimulation pulses form a pulse train including (i) an initial selective-arrest phase for the large-diameter fibers in the vicinity of selected electrodes; (ii) followed by a charge-balanced phase where a charge-balanced alternating current (AC) is applied between the same or other selected electrodes; and (iii) a therapy phase where the charge-balanced alternating current (AC) is briefly unbalanced to deliver nerve stimulation therapy pulses, with the pulse train returning to the charge-balanced phase in between therapy pulses.

24 Claims, 12 Drawing Sheets

(56) References Cited

U.S. PATENT DOCUMENTS

| | | |
|---|---|---|
| 2005/0149148 A1 | 7/2005 | King |
| 2008/0058878 A1 | 6/2008 | King |
| 2008/0058888 A1 | 6/2008 | King |
| 2008/0300657 A1 | 12/2008 | Stultz |
| 2010/0191311 A1 | 7/2010 | Scheiner et al. |
| 2010/0241190 A1* | 9/2010 | Kilgore ................. A61N 1/205 607/48 |
| 2011/0040353 A1* | 2/2011 | Gerber .............. A61M 5/14276 607/59 |
| 2011/0106214 A1* | 5/2011 | Carbunaru ......... A61N 1/36128 607/60 |
| 2014/0046407 A1 | 2/2014 | Ben-Ezra et al. |

OTHER PUBLICATIONS

Baratta et al. "Orderly Stimulation of Skeletal Muscle Motor Units with Tripolar Nerve Cuff Electrode", *IEEE Transactions on Biomedical Engineering*, vol. 36, No. 8, pp. 836-843, Aug. 1989.

* cited by examiner

DEVICE AND METHOD FOR SELECTIVE NERVE STIMULATION

CROSS-REFERENCE TO RELATED APPLICATIONS

This application claims priority under 35 USC § 119(e) to U.S. Provisional Patent Application 62/150,865 filed 22 Apr. 2015, the entirety of which is incorporated by reference herein.

FIELD OF THE INVENTION

The invention relates to an implantable pulse generator (IPG) connected or connectable to a stimulation lead having stimulation electrodes for stimulation pulse delivery, and that includes a stimulation unit and control unit configured to generate electric stimulation pulses for nerve stimulation, e.g. vagus nerve stimulation (VNS). The invention further relates to a method for nerve stimulation, e.g. vagus nerve stimulation (VNS).

BACKGROUND OF THE INVENTION

Vagus nerve stimulation (VNS) recently emerged as a potential progression-preventing and treatment option for congestive heart failure (CHF) patients. Experimental data have demonstrated that stimulation of the vagus nerve at the cervical level is able to reverse ventricular remodeling of the failing heart. There is also evidence that increasing parasympathetic activity may stimulate the production of nitric oxide, and reduce the devastating inflammatory process involved in heart failure. Present VNS devices for CHF involve an implanted nerve cuff electrode that connects via wires to an implantable pulse generator (IPG) in the patient's chest. In some devices, a standard pacemaker sensing lead in the ventricle provides cardiac sensing for synchronous delivery of VNS pulses in the cardiac refractory period, although other devices operate asynchronously to the cardiac cycle. CHF treatment via stimulation of both the right and left vagus nerves is known.

To reduce side effects when treating CHF, it is desirable to selectively stimulate a vagus nerve region with a majority of parasympathetic cardiac fibers, while minimizing the possible stimulation of large-diameter fibers that innervate the pharynx and the larynx.

U.S. Pat. No. 5,199,430 describes use of a nerve cuff electrode and quasi-trapezoidal (QT) pulses to selectively initiate action potentials adjacent to a central electrode, and to block the propagation of action potentials adjacent to the end electrodes along the larger-diameter nerve fibers, but not the smaller-diameter nerve fibers.

U.S. Pat. No. 7,389,145 describes a specific electrical stimulus waveform that can be applied to block nerve activity. It consists of a first sub-threshold cathodic phase immediately followed by an anodic phase, i.e., when the cathodic current reaches zero, the pulse is reverted with a non-zero amplitude. This biphasic pulse is repeated continuously, and the amplitude may be increased to block other smaller-diameter fibers as desired.

US Patent Appl'n Publ'n. 2010/0191311 describes the use of a nerve cuff electrode and two stimulation trains, a low-frequency train and a high-frequency one, delivered either using the same or different electrodes. The low frequency train can be used to recruit the desired cardiac fibers for treatment while the activity of certain nerve branches (for example, those innervating the larynx or pharynx), are blocked via the high-frequency train. An identical technique, showing reverse nerve fiber recruitment, was disclosed by Baratta et al. in 1989, although not in the vagus nerve (Baratta et al. "Orderly Stimulation of Skeletal Muscle Motor Units with Tripolar Nerve Cuff Electrode", IEEE Transactions on Biomedical Engineering, vol. 39, no. 8, pp. 836-843, August 1989).

Nerve cuffs which use ring electrodes, which have been in use since the early 1970s, are illustrated in (for example) U.S. Pat. No. 8,615,294.

SUMMARY OF THE INVENTION

The invention seeks to provide improved nerve stimulation, in particular an improved implantable pulse generator (IPG) and an improved method for vagus nerve stimulation (VNS).

An exemplary version of the invention involves an IPG connected or connectable to a stimulation lead having stimulation electrodes for delivery of stimulation pulses. The IPG includes a stimulation unit configured to generate electric stimulation pulses for nerve stimulation, and a control unit configured to trigger delivery of generated electric stimulation pulses via selected electrodes of the stimulation electrodes. The electric stimulation pulses form a pulse train including:

i) an initial selective-arrest phase for the large-diameter fibers in the vicinity of the selected electrodes;

ii) followed by a charge-balanced phase where a charge-balanced Alternating Current (AC) is applied between the same or other selected electrodes;

iii) and a therapy phase wherein the charge-balanced AC is briefly unbalanced to effectively deliver nerve stimulation therapy pulses, returning to charge-balanced operation in between therapy pulses.

Preferably, the stimulation electrodes include at least one ring electrode, and contacts that are electrodes with a smaller contact surface than the ring electrode. The stimulation electrodes may also or alternatively include at least two ring electrodes that are axially spaced from each other, and wherein the contacts are arranged between the at least two ring electrodes.

The control unit of the implantable pulse generator may be configured to have any one or more of the following features:

i) to make the selection of one or more electrodes of the stimulation electrodes;

ii) to trigger a pulse train for nerve stimulation therapy that is time duty-cycled;

iii) to trigger bipolar stimulation between two of the contacts, or a contact and at least one ring;

iv) to terminate nerve stimulation therapy by interruption of the pulse train.

The control unit of the implantable pulse generator may also or alternatively be configured to trigger delivery of a pulse train effecting a passive charge-balancing phase involving short circuiting of the selected active contact(s) and ring(s) as required during the pulse train, and immediately after termination of the nerve stimulation therapy. The charge-balancing period may involve two stages with different contact(s) and ring(s).

The stimulation unit of the implantable pulse generator may be configured to generate a kHz alternating current (AC), wherein the stimulation unit includes or is connected to a low-Q Class-E switched amplifier for generating the kHz alternating current (AC).

The implantable pulse generator may be configured to effect the initial selective-arrest phase of the s pulse train by rectification of the kHz alternating current (AC) with a suitable envelope, in particular an envelope approximating a quasi-trapezoidal (QT) pulse. Preferably, the selective-arrest phase is effected by means of pre-depolarization sub-threshold pulses.

The invention also involves a method for selective neural stimulation, in particular for vagus nerve to stimulation (VINS), wherein the method includes providing a stimulation pulse train, the pulse train including stimulation pulses that are configured to effect:

i) an initial selective-arrest phase for the large-diameter fibers in the vicinity of selected electrodes;

ii) followed by a charge-balanced phase where a charge-balanced Alternating Current (AC) is applied between the same or other selected electrodes;

iii) and where the charge-balanced AC is briefly unbalanced to effectively deliver nerve stimulation therapy pulses, returning to charge-balanced operation in between therapy pulses.

The initial selective-arrest phase for the large-diameter fibers is preferably achieved by hyperpolarization of such fibers. In a following phase, selective arrest is achieved by sub-threshold membrane depolarization, causing inactivation of sodium channels while avoiding action potential generation. The transition from hyperpolarization to high-frequency induced sub-threshold depolarization is beneficial, as it enables conduction block while avoiding initial supra-threshold depolarization at the onset of blocking stimulation.

The nerve stimulation therapy may be delivered to the vagus nerve with the initial selective-arrest phase for the large-diameter fibers being delivered to nerve fibers that innervate the pharynx and the larynx.

Thus, preferred versions of the invention provide an implantable device and method for cervical vagus nerve stimulation (VNS), with the capability of selectively stimulating regions of a vagus nerve with a majority of parasympathetic cardiac fibers while minimizing possible stimulation of the large-diameter fibers that innervate the pharynx and the larynx (should they be present). The invention may be particularly suitable for the management of congestive heart failure (CHF). The implantable pulse generator (IPG), which is configured to be implanted in the patient's chest, preferably includes or is connected to a multi-contact nerve cuff electrode via a stimulation lead. The nerve cuff electrode may have at least three contacts which are circumferentially distributed at equal increments and located towards the center of the cuff, and may also have at least one ring electrode near its edge.

The invention recognizes that cervical vagus nerve stimulation (VNS) by means of an implanted cuff electrode may suffer from unwanted recruitment of large-diameter fibers which may translate into undesired side effects such as voice hoarsening, coughing, shortness of breath, and pain in the neck area during therapy delivery for cardiovascular effects. The invention provides a solution which may limit the recruitment of large-diameter fibers to a single event, at the beginning of each VNS therapy pulse train, thus minimizing such unwanted side effects.

Nerve stimulation therapy, in particular VNS, may be time duty-cycled and preferably delivered by bipolar stimulation between two of the contacts, or between a contact and at least one ring. Given the limited nerve cuff length available for cervical implantation, undesired recruitment of large-diameter fibers (during VNS therapy) may be minimized by a pulse train composed of:

i) an initial selective-arrest phase for the large-diameter fibers caused by stimulation applied between a selected contact and ring(s);

ii) followed by a charge-balanced phase where a charge-balanced alternating current (AC) is applied between a selected contact and ring(s), or alternatively between contacts, in which case ring(s) is(are) disconnected;

iii) and where such AC is briefly unbalanced to effectively deliver VNS therapy pulses, returning to charge-balanced operation in between therapy pulses.

Accordingly, laryngeal and pharyngeal (large-diameter) nerve fibers are arrested by the first selective-arrest phase of the stimulation train, e.g., by using a stimulation signal with quasi-trapezoidal (QT) form, which can be generated by the envelope of the rectified AC signal. Arresting activity by hyperpolarization of large-diameter fibers prevents over-muscle response which would otherwise be evoked by the high-frequency stimulation for blocking such fibers in the subsequent charge-balanced phase. Then, stimulation is applied using charge-balanced, high frequency (preferably kH range) AC for blocking large-diameter fiber activity, wherein the high frequency signal is modulated in a way that both VNS for cardiovascular effects and blocking of the laryngeal and pharyngeal nerve fibers are promoted (e.g., unbalance of the high frequency signal generates VNS).

Therapy may be terminated by interruption of the pulse train. A passive charge-balancing phase may follow for neutrality purposes, involving short-circuiting of the selected active contact(s) and/or ring(s). A similar balancing phase may be required during the pulse train delivery. This charge-balancing phase may involve two stages with different contact(s) and/or ring(s).

In a preferred version of the invention, a single multi-phase waveform pulse train is utilized including an initial phase with a net charge component to arrest action potentials of large-diameter fibers, which transitions into a continuous, charge-balanced AC waveform (preferably 32,768 Hz or submultiple down to hundreds of Hz) to prevent such fibers from conducting after the conclusion of the selective-arrest phase. Temporary unbalancing of the AC waveform, or injection of larger cathodic pulses during a short quiescent period of the waveform, is utilized to induce a net cathodic impulse and recruit smaller-diameter, unblocked cardiac fibers for therapy. Once the block is established, the AC waveform may be switched off (e.g. <10 ms) without affecting the blocking effect.

In a preferred version, a bipolar cuff arrangement with a central cathode (a contact) flanked by an anode (preferably an edge ring or other anode proximal to the vagus heart innervation) implement the selective-arrest phase of the large-diameter fibers. A suitable "pseudo" pulse is utilized during this phase, which may be implemented by injecting a rectified version of the AC waveform with an envelope approximating a desired continuous equivalent pulse. Cardiac fibers may be stimulated during this selective-arrest phase. Following its termination, the cuff configuration may automatically be switched to bipolar stimulation between the cathode contact and a contact selected to work as an anode (preferably one different from the ring anode), and the stimulation is transitioned into a continuous, charge-balanced AC waveform with an amplitude that prevents the large-diameter fibers from firing action potentials. To deliver therapy pulses, i.e. recruit cardiac fibers, the AC waveform may be temporarily unbalanced (e.g. rectified for tens to hundreds of μs) and returned to charge-balanced operation at the end of a therapy pulse. VNS therapy can thereafter be terminated without triggering a large-diameter fiber action potential. A passive charge-balancing period (ms to tens of ms range), utilizing the active contact(s) and/or ring(s) involved, may be performed during the AC-waveform quiescent period, and immediately after pulse train termination. Such a charge-balancing phase may be done in two different stages involving different contact(s) and/or ring(s).

Preferably, a kHz alternating current (AC) is utilized and generated by a switched amplifier, in particular a low-Q Class-E amplifier where efficiency is traded for harmonic distortion.

Given that linearity is not required for kHz AC nerve stimulation, a Class-E amplifier is useful for the implementation of the stimulation circuitry. To reduce the number of components, a single inductor, single capacitor Class-E amplifier is proposed with DC blocking capacitors in series with each contact and ring. Analog switches allow connecting/disconnecting the different contacts and ring(s) and implementing half-way rectification via some switches' parasitic diodes. The Class-E amplifier may be powered from battery voltage, or from voltages generated from it, or from other regulated voltages when alternative powering is utilized in the implantable pulse generator (IPG).

The selective-arrest phase may be implemented by rectification of the kHz alternating current (AC) with a suitable envelope, e.g. an envelope approximating a quasi-trapezoidal (QT) pulse (hereinafter referred as pseudo QT). Alternatively, pre-depolarization sub-threshold pulses are instead utilized to implement the selective-arrest phase.

In an alternative version, an H-bridge with an arbitrary waveform generator is instead utilized to implement the pulse train.

The automatic selection of the best contact(s) or contact ring(s) for therapy, as well as other aspects of closed-loop operation such as intrathoracic far-field electrogram (ff-EGM) recording and processing, and communication with an external programmer or bedside patient messenger, are further features that may be implemented in the invention.

As mentioned before, the invention provides a solution which may limit the recruitment of large-diameter fibers to a single event, or to a no-action-potential event, at the beginning of each VNS therapy pulse train, thus minimizing unwanted side effects. Further advantages and features of the invention will be apparent from the remainder of this document in conjunction with the associated drawings.

DETAILED DESCRIPTION OF EXEMPLARY VERSIONS OF THE INVENTION

Figure 1:
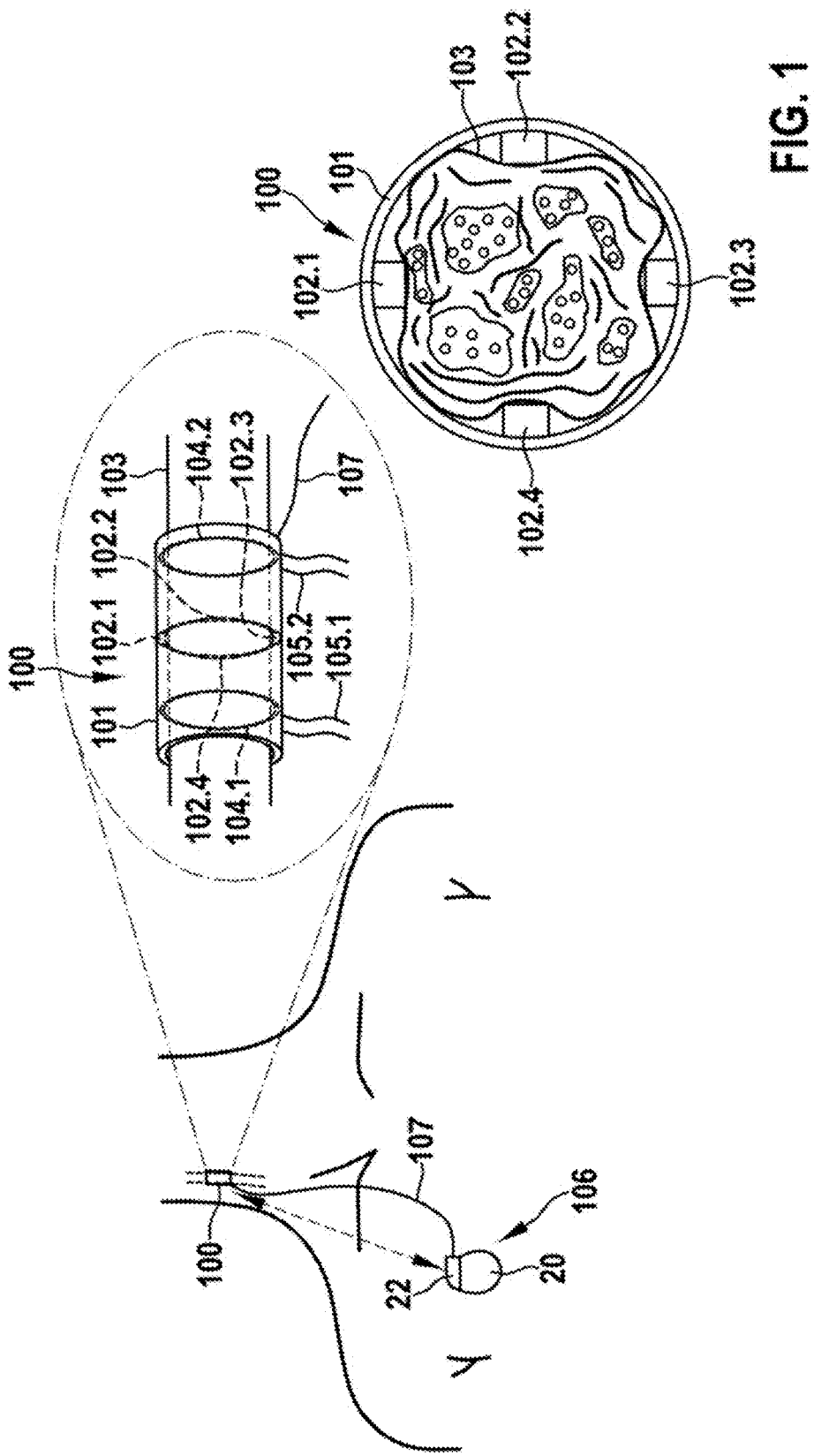
FIG. 1 shows an exemplary version of the invention.

FIG. 1 shows an exemplary version of the invention having a nerve cuff electrode 100, an implantable pulse generator (IPG) 106 and an implantable electric lead 107. The nerve cuff electrode 100 may be constructed using a silicone rubber tube 101, with exposed contacts 102.1, 102.2, 102.3, and 102.4 being centered along the length of the tube 101, and distributed about the circumference of its interior wall (with these contacts being individually and collectively referred to as contact(s) 102). The tube 101 of the nerve cuff electrode 100 also includes at least one ring 104.1 situated towards the edge of the electrode 100 proximal to where the vagus nerve innervates the heart, with a second distal ring 104.2 also preferably being included in the exemplary cuff electrode 100 of FIG. 1 (and with the rings being individually and collectively referred to as ring(s) 104). In a third preferred version, the nerve cuff electrode 100 may only include ring 104.1 and the contacts 102 may be off-centered. While the contact(s) 102 are preferably centered between the rings 104, they need not be, particularly where only a single ring 104.1 is included. The contacts 102 and rings 104 are all in contact with the surface of the right vagus nerve 103, and serve as vagus nerve stimulation electrodes.

The cuff 100 may be self-coiling, or it may include other closing mechanisms such as a piano hinge with a nylon suture (not shown). Biocompatible strings 105 may be provided on the outer wall of the cuff 100 to allow easy opening for implantation around the vagus nerve 103. The contacts 102 are preferably formed of Pt/Ir, or of fractal Ir for higher charge-injection capacity, and have area of (for example) 2 mm². The ring(s) 104, which are preferably formed of the same or other suitable materials, need not have annular conductive areas, and could be formed of individual circumferentially-distributed segmented electrodes so that when they are driven in synchrony, their provided electrical field effectively matches that formed by a complete ring electrode.

The cuff 100 is connected to IPG 106, which may be located in the patient's chest area via a subcutaneously-implanted isolated multi-wire lead 107 which provides an electrical connection to the contacts 102 and ring(s) 104.

Figure 2:
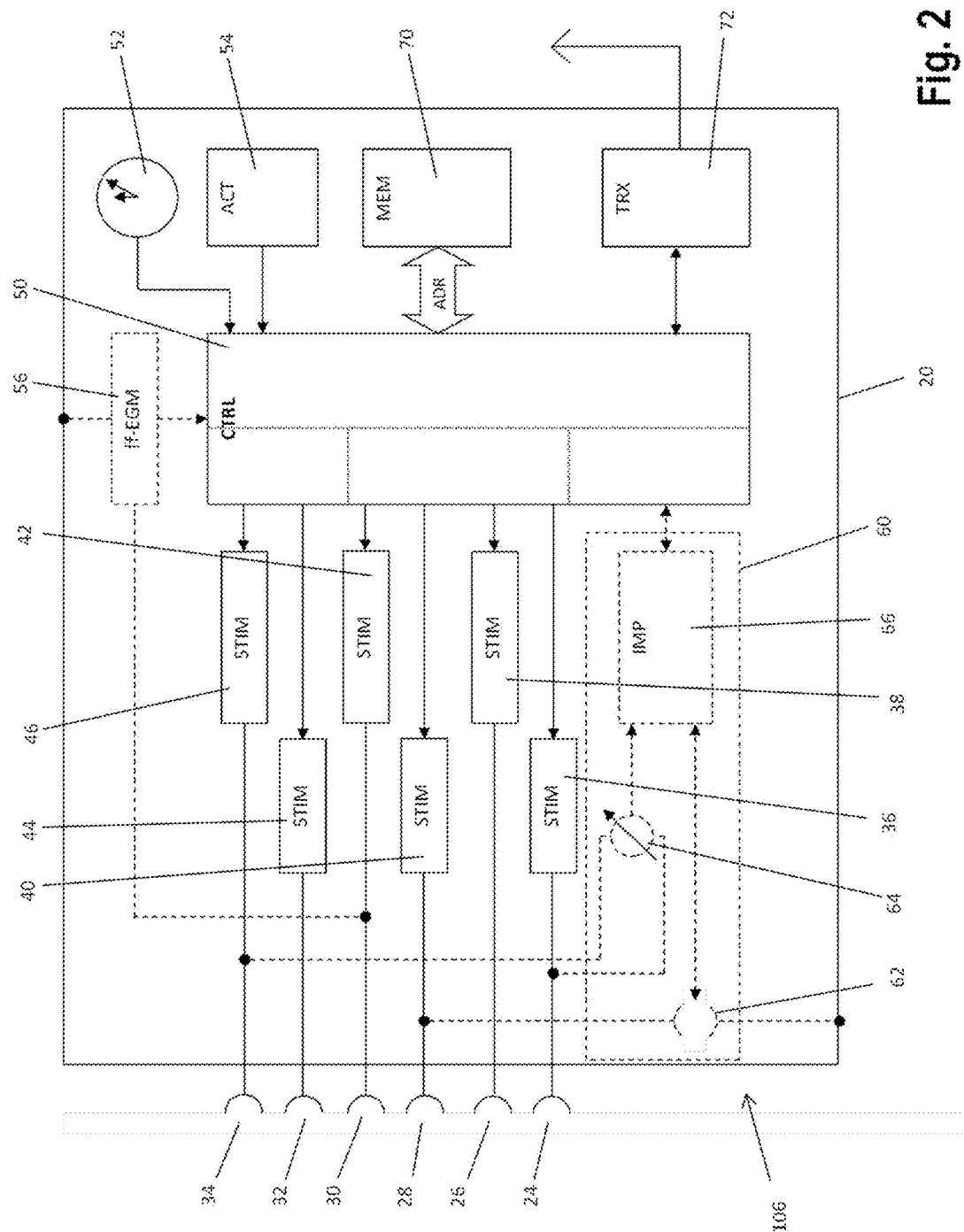
FIG. 2 is a schematic diagram of exemplary components of an implantable pulse generator (IPG).

FIG. 2 is a schematic diagram of exemplary components of an implantable pulse generator (IPG) 106. The IPG 106 includes a case 20 having a header 22 (see FIG. 1) for connection of the electric lead 107. The header 22 includes a number of connectors 24, 26, 28, 30, 32 and 34—at least five, corresponding to the contacts 102 and ring(s) 104—that can electrically connect to connectors of the electrical lead 107. Thus, an electric connection can be made between the connectors 24, 26, 28, 30, 32 and 34 of the IPG 106 and the electrodes (contacts and rings) 102 and 104 of the nerve cuff electrode 100.

Within the IPG case 20, one or more stimulation units (here five units) 36, 38, 40, 42, 44 and 46 are respectively electrically connected to the connectors 24, 26, 28, 30, 32 and 34, and are configured to generate stimulation pulses and to deliver such stimulation pulses via a respective connector 24, 26, 28, 30, 32 and 34. Instead of one stimulation unit for each connector (and thus for each electrode 102 and 104), a single stimulation unit can be provided with a switch matrix whereby all stimulation pulses can be generated by the single stimulation unit, and can be delivered to selected electrodes 102 and 104 via the switch matrix. As another option, all contacts 102 are switched in parallel to each other—no selection of individual contacts 102 for delivery of stimulation pulses is possible—and thus only one connector and one stimulation unit is needed.

In the version of FIG. 2, a control unit 50 is connected to each stimulation unit 36, 38, 40, 42, 44 and 46 to control generation, and trigger delivery, of stimulation pulses by stimulation units 36, 38, 40, 42, 44 and 46. The stimulation pulses generated and triggered by each stimulation unit 36, 38, 40, 42, 44 and 46 are tailored for vagus nerve stimulation (VNS).

The control unit 50 is also connected to a time signal generator 52 that supplies a time base to control unit 50.

Further, an activity sensing unit 54 may be provided for sensing movements of the patient via movements of the IPG 106, preferably in three spatial dimensions (e.g., via a 3-axis accelerometer). The resulting activity signal can be provided by the activity sensor 54 to the control unit 50.

The control unit 50 may also be connected to a far-field electrogram (ff-EGM) sensing unit 56 configured to generate a ff-EGM signal representing a far-field electrogram. In order to record such an ff-EGM signal, the far-field sensing unit 56 is connected to at least one of connectors 24 to 34, and thus to one of the electrodes 102 or 104 of the nerve cuff electrode 100. Another input of the ff-EGM sensing unit 56 is connected to the IPG case 20. Thus, the ff-EGM sensing unit 56 can sense voltages between at least an electrode 102 or 104 and the IPG case 20 that result from electric potentials caused by a patient's heart activity. The far-field electrogram sensing unit 56 is configured to supply a ff-EGM signal to the control unit 50, with the ff-EGM signal allowing determination of heart rate and other heart activity.

The control unit 50 may further be connected to an impedance measuring unit 60 that includes a constant current source 62 for generating and delivering biphasic impedance measuring pulses. The current source 62 may electrically connect to the IPG case 20 and to at least one of the connectors 24, 26, 28, 30, 32 and 34, and thus to at least one of the electrodes 102 or 104 of the nerve cuff electrode 100. The impedance measurement unit 60 further includes a voltage sensing unit 64 configured to measure a voltage difference between at least one electrode 102, 104 of nerve cuff electrode 100 and the IPG case 20, or between at least two electrodes 102, 104, in response to delivery of current pulses by the current source 62. The current source 62 and the voltage sensing unit 64 are connected to an impedance determination unit 66 of the impedance measurement unit 60, wherein the impedance determination unit 66 is configured to generate an impedance signal depending on the voltages measured by the voltage sensing unit 64, and to supply the impedance signal to the control unit 50. The impedance signal generated by the impedance measurement unit 60 allows assessment of the status of the electrodes 102, 104.

The control unit 50 may further be connected to a memory unit 70 that may store signals recorded by the control unit 50, and/or programs that control the operation of the control unit 50.

In order to wirelessly communicate recorded signals to an external device or to receive program instructions, a telemetry unit 72 may also be provided in connection with the control unit 50.

Figure 3:
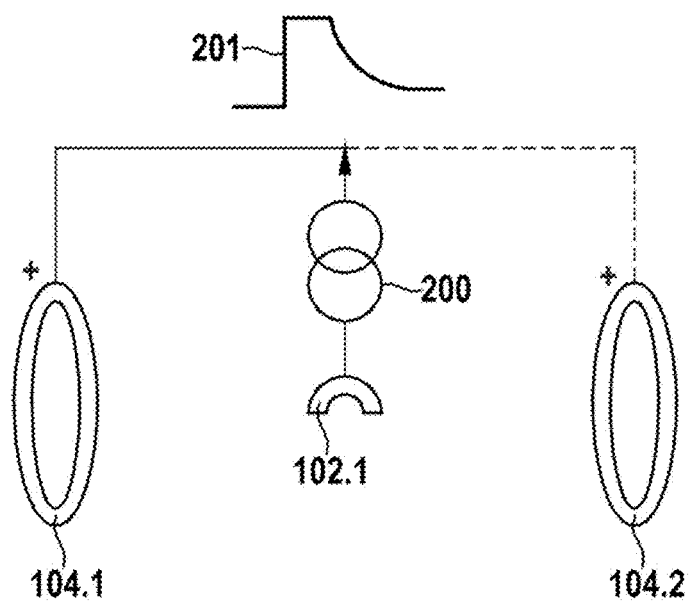
FIG. 3 conceptually illustrates the connection for implementing the selective-arrest phase when vagus nerve stimulation (VNS) therapy is to be delivered.

FIG. 3 conceptually describes the preferred connection for implementing the selective-arrest phase when VNS therapy is to be delivered. Assume the contact 102.1 has been designated as the preferred cathode, and the ring 104.1 as the anode. The control unit 50 (and an associated stimulation unit) injects an electrical pulse 200 (preferably current-based) that exits contact 102.1. The electrical pulse 200 may have, for example, a quasi-trapezoidal (QT) envelope 201, i.e. a square leading edge, a plateau pulse width (typically 50 to 500 μs), followed by an exponential trailing phase with a fall (90% to 10%) of similar duration to the plateau pulse width. Other cathode/anode arrangements are possible; for example, both rings 104 may be utilized as anodes for therapy.

Figure 4:
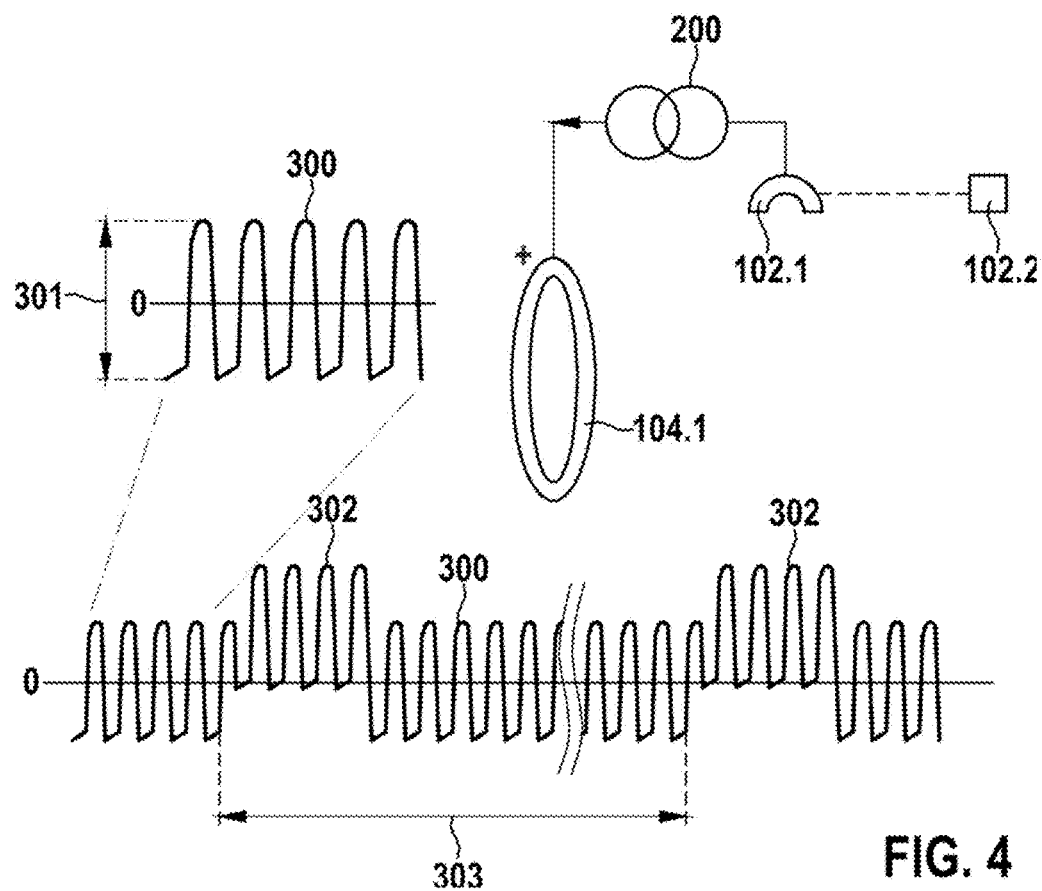
FIG. 4 conceptually describes the connection after the selective-arrest phase is completed.

Once the selective-arrest phase is completed, the configuration of FIG. 3 may be automatically switched by the control unit 50 to the one shown in FIG. 4, assuming that VNS therapy is to continue with the ring 104.1 as the anode (and with the phantom/dashed line arrangement assuming, as an example, that VNS therapy is to be delivered between cathode contact 102.1 and anode contact 102.2). Regardless of the chosen configuration, the control unit 50 will continue outputting electrical pulses 200 between an anode and the selected cathode. The current 200 may now transition to a charge-balanced, preferably non-pure-sinusoidal waveform 300 of sufficient amplitude 301 (referred to as "baseline" amplitude) to prevent large-diameter vagus nerve fibers from firing action potentials. To deliver VNS therapy, the sinusoidal waveform 300 is periodically briefly unbalanced (e.g., rectified), creating the pseudo pulses 302, and brought back to baseline between periods of imbalance. This envelope change may have different shapes for stimulation, and is preferably repeated with a period 303 typically between 10 to 100 ms during therapy delivery.

Figure 5:
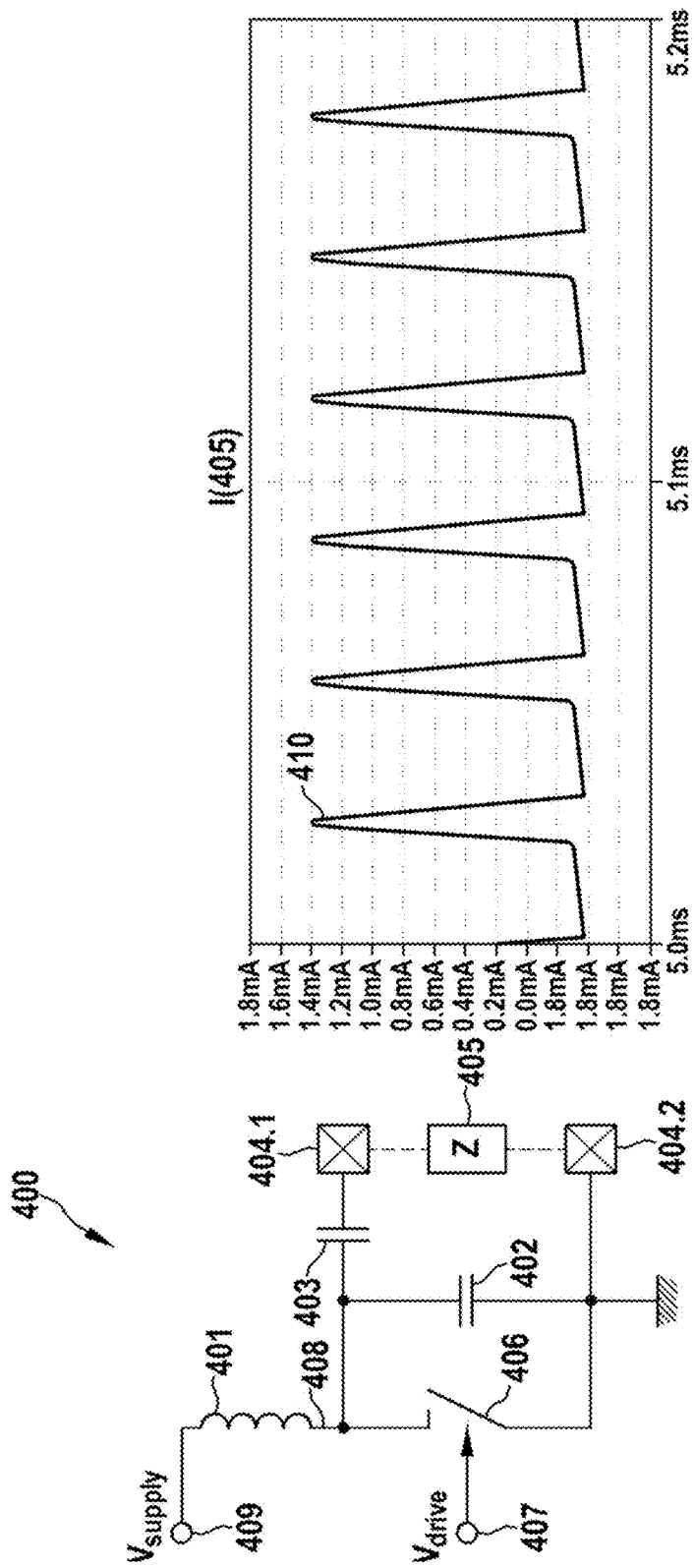
FIG. 5 is a schematic representation of the stimulation circuitry for delivery of VNS therapy.

FIG. 5 is a schematic representation of the preferred stimulation circuitry for delivering VNS therapy. This circuit 400 is a switched-mode Class-E amplifier with a parallel LC circuit having inductor 401 and capacitor 402. A DC blocking capacitor 403 may be placed in series with the electrodes 404 in contact with tissue (the impedance between them is represented at 405 by Z). Only two electrodes 404 are shown to describe the circuit; these may be any contact 102 or ring 104 (with operation with multiple electrodes 404 being discussed later, and shown in FIG. 6).

Capacitor C 402 includes the parasitic capacitance of the analog switch 406. This switch 406 is driven by signal $V_{drive}$ 407 in such a way as to provide switching between its on-state and off-state operation modes. As a result, the voltage in node 408 is determined by the transient response of the LC load network (401, 402) when the switch 406 is off. For superior operation, $V_{drive}$ 407 may have a 50% duty cycle. The circuit 400 is powered by $V_{supply}$ 409.

Assuming the analog switch 406 is ideal (i.e., has zero saturation voltage, zero saturation resistance, infinite off-state resistance, and its switching action is instantaneous and lossless), and that capacitor C 402 is independent of node voltage 408 and assumed linear, the optimum values for L 401 and C 402 can be derived from:

$$L = 0.41 \frac{Re(Z)}{w} \quad C = \frac{1.025}{w \, Re(Z)}$$

where Re(Z) is the resistive part of the electrode(s)-tissue impedance 405 and w is the angular frequency of $V_{drive}$ 407.

Since $V_{drive}$ 407 is preferably in the kHz range, Z 405 may be primarily resistive. At 32,768 Hz for example, Re(Z) may be on the order of 1,000Ω, and the equations above determine a value of approximately 2 mH and 5 nF for inductor 401 and capacitor 402 respectively. Analog switch 406 may be an NMOS transistor. The circuit 400 generates a current through Z 405 with shape 410 when $V_{supply}$ 409 is 1.2 V.

Figure 6:
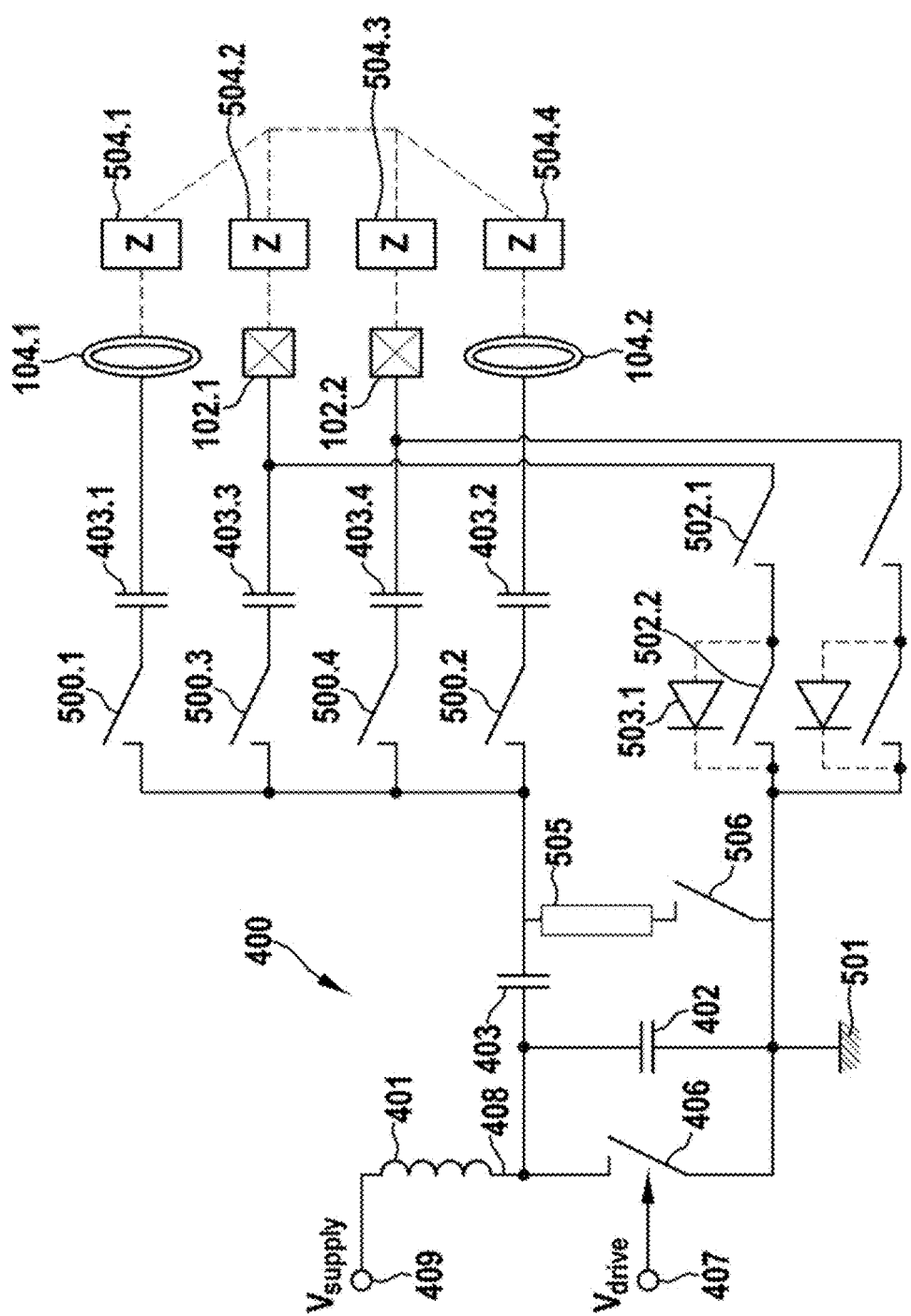
FIG. 6 illustrates an extension of the circuit in FIG. 5 for operation with multiple electrodes.

With the addition of extra analog switches, the circuit of FIG. 5 may be expanded as shown in FIG. 6 to implement a preferred pulse train for VNS therapy. The rings 104.1 and 104.2 are in series with DC blocking capacitors 403.1 and 403.2, and may connect to node 408 via analog switches 500.1 and 500.2 respectively. Contacts 102.1 and 102.2—being considered as examples—may also connect to node 408 through similar analog switches 500.3 and 500.4 and DC blocking capacitors 403.3 and 403.4 respectively. Contact 102.1 may also connect to the circuit ground 501 via analog switches 502.1 and 502.2. The parasitic diode 503.1 of the analog switch 502.2 is shown as it is utilized in the implementation of the selective-arrest phase of the pulse train in a preferred version discussed below. Similar components (not all of them shown) connect the remaining contacts. Electrode-tissue impedances from the rings 104.1, 104.2, and the contacts 102.1, 102.2 are represented by Z blocks 504.1, 504.2, 504.3, and 504.4. Finally, resistor 505 and analog switch 506 are utilized for charge-balancing, as will also be described later.

Figure 7:
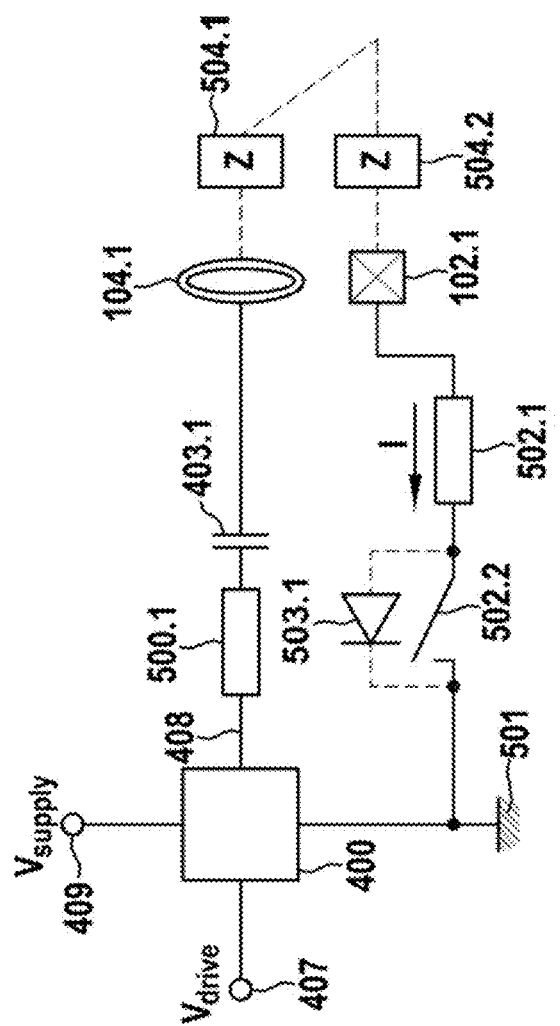
FIG. 7 shows a circuit connection for delivering a selective-arrest phase using a pseudo quasi-trapezoidal (QT) pulse.

FIG. 7 shows the preferred circuit connection of FIG. 6 for delivering a selective-arrest phase using a pseudo quasi-trapezoidal (QT) pulse. In this configuration, the analog switch 500.1 is closed, which connects the ring 104.1 to the node 408 through the DC blocking capacitor 403.1. On the other hand, analog switch 502.1 is closed, connecting contact 102.1 to circuit ground 501 through the parasitic diode 503.1 of the analog switch 502.2 (which remains open). The switched-mode Class-E amplifier circuit 400 is connected to the node 408 and to the circuit ground 501. When $V_{drive}$ 407 drives analog switch 406 (inside 400, shown in FIG. 6) and $V_{supply}$ 409 is ramped up linearly for 200 μs from 1.2 V to a final value of 2.0 V, and linearly ramped down reaching 1.2 V at 500 μs, the current I exiting contact 102.1 (shown across 500.1) and flowing through tissue has the shape shown in FIG. 8.

Figure 8:
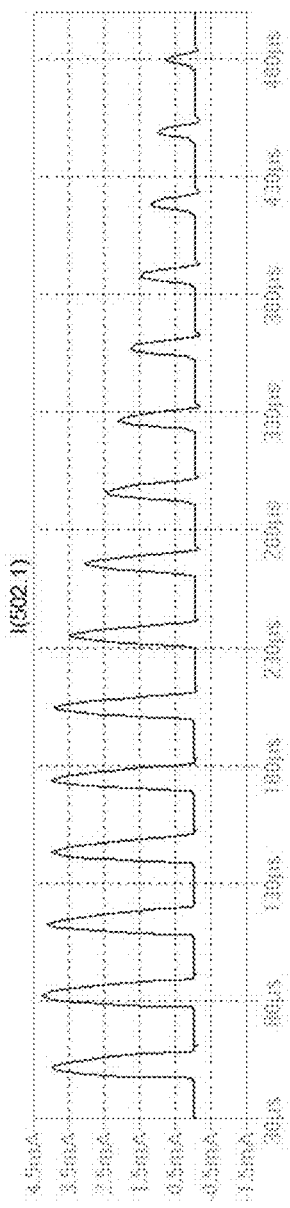
FIG. 8 illustrates the shape of the current flowing through tissue exiting a stimulation contact.
Figure 9:
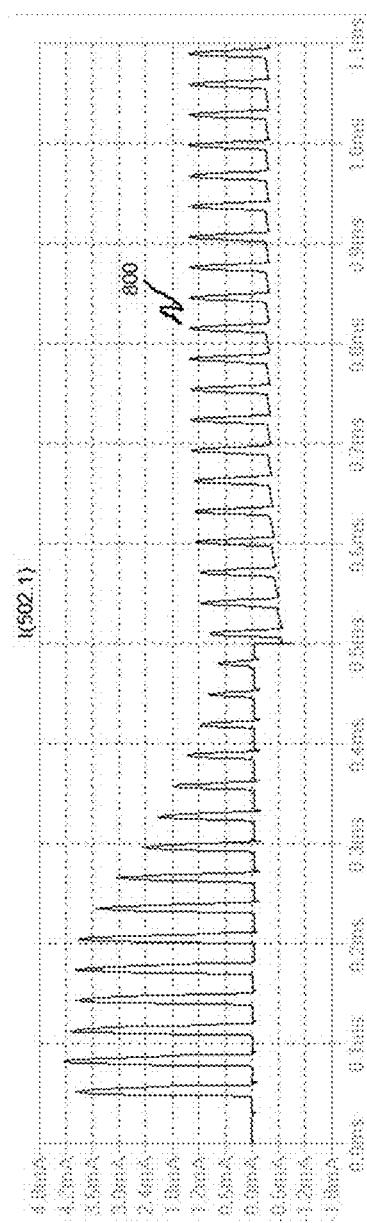
FIG. 9 illustrates a waveform that occurs when the rectifying characteristic of the current flowing through tissue disappears and transitions to a steady-state, charge-balanced alternating current (AC) waveform.

At the end of the selective-arrest period of FIG. 8, switch 502.2 is closed. As a result, the rectifying characteristic of the current I (at 502.1) flowing through tissue will disappear, and will transition (after approximately 150 μs using the foregoing arrangement) to the steady-state, charge-balanced alternating current (AC) waveform 800 shown in FIG. 9. The amplitude of this waveform 800 prevents the largest diameter fibers from conducting. $V_{drive}$ 407 is uninterrupted and $V_{supply}$ 409 is maintained at 1.2 V. Once block is established, the waveform 800 may be switched on and off as temporary interruptions will not affect the blocking effect on the large-diameter fibers. During the off time, passive charge-balancing may be performed for neutrality purposes as desired.

Figure 10:
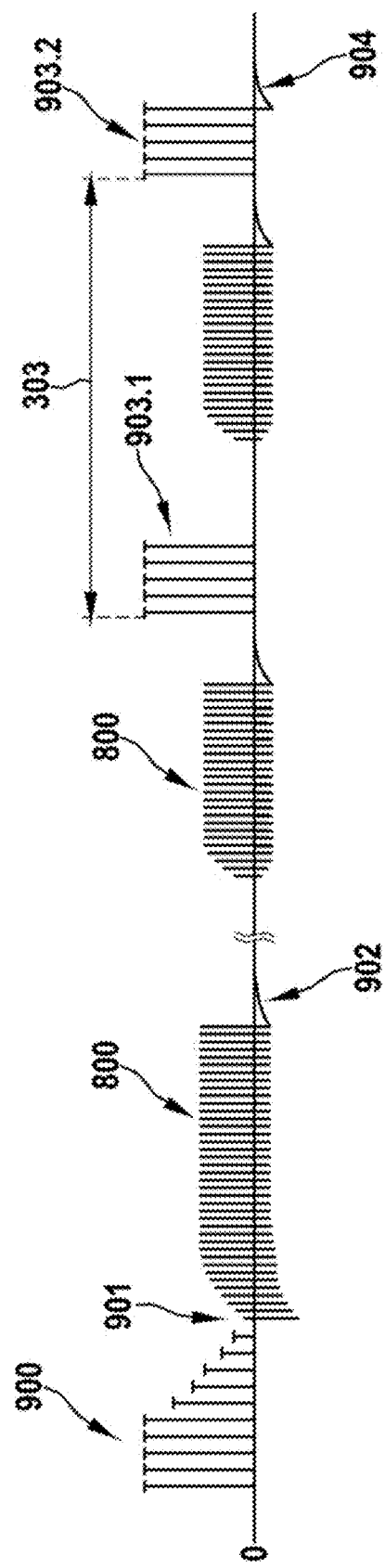
FIG. 10 schematically shows a typical VNS therapy train.

To deliver therapy, switch 502.2 may be opened to create a pseudo pulse similar to the creation of the selective-arrest phase. FIG. 10 schematically shows a typical therapy train that starts with the selective-arrest phase 900 and transitions (region 901) to a steady-state, charge-balanced alternating current (AC) waveform 800. Once block of the large-diameter fibers is achieved, the AC waveform 800 may be turned off, and the charge accumulated in the DC blocking capacitors and the electrode-tissue capacitances may be bled off via a passive charge-balancing phase 902. The AC waveform 800 may be turned on and off while maintaining the blocking effect. Therapy can be delivered by unbalancing the AC waveform 800. It may be on or off when a therapy pulse 903 needs to be delivered. Therapy pulses may have different envelopes with respect to the selective-arrest phase 900. For example, in FIG. 9 these pulses 903 have a rectangular envelope. At the end of the VNS therapy pulses, a global balancing phase 904 takes place for neutrality purposes.

Figure 11:
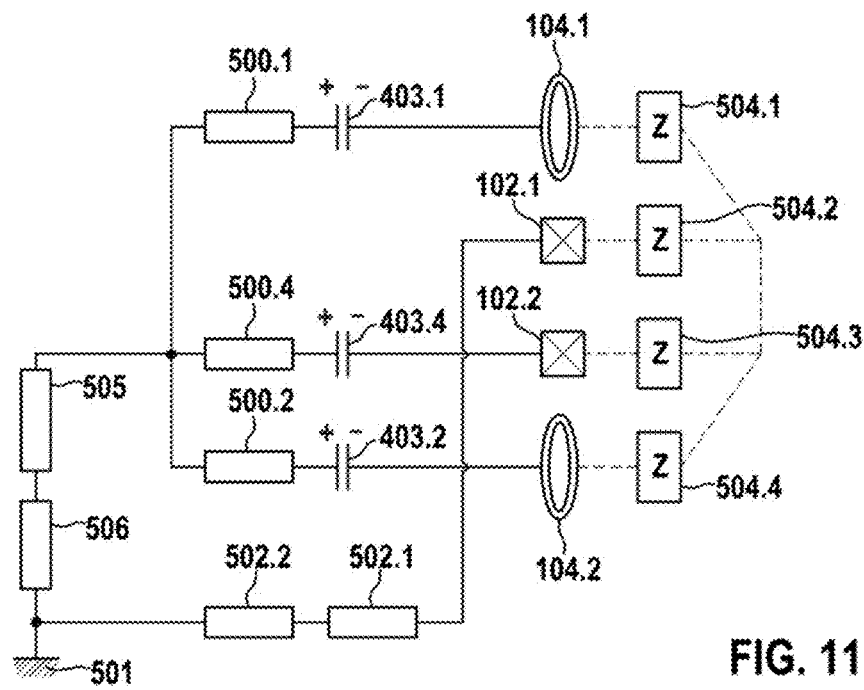
FIG. 11 shows a circuit connection for achieving charge-balancing.

To initiate a passive charge-balancing phase 902, 904, the active analog switches that connect the participating contact(s) 102 and ring(s) 104 are opened, $V_{supply}$ 409 and $V_{drive}$ 407 are brought to circuit ground voltage 501, and analog switch 506 (see FIG. 6) is closed. This will dissipate the s energy left in L 401 and C 411 through resistor 505. Charge-balancing may then be achieved with the circuit connection of FIG. 11. Analog switches 500.1, 500.2, 502.1, 502.2, 506, and 500.4 (assuming ring 104.2 and contact 102.2 participated in the therapy) are closed, discharging the voltage accumulated in the DC blocking capacitors 403.1, 403.2 and 403.4, and in the electrode-tissue capacitances of 504.1, 504.2, 504.3 and 504.4, through resistor 505 (which is preferably in the kΩ range). This charge-balancing period may be implemented in two stages: one corresponding to the selective-arrest phase (where in the foregoing arrangement only analog switches 500.1, 500.2, 502.1, 502.2 and 506 are closed for a finite period of time, preferably ms to tens of ms range), and another one where analog switches 500.1 and 502.2 are opened and 500.4 closed instead for another finite period of time (assuming contact 102.2 was utilized as the anode for therapy).

Figure 12:
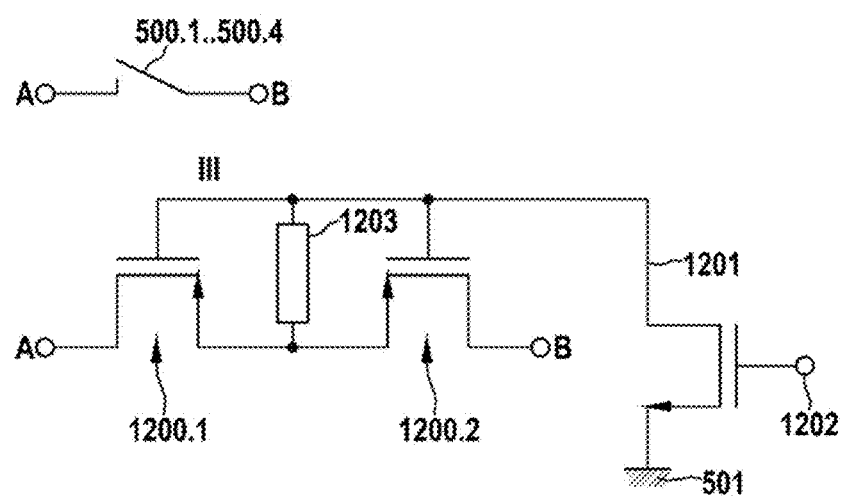
FIG. 12 shows a version wherein analog switches are implemented with back-to-back PMOS transistors.

Analog switches 500.1 through 500.4 (and the equivalents not drawn for the other contacts) may be implemented with back-to-back PMOS transistors 1200.1 and 1200.2 as shown in FIG. 12, enabled by NMOS transistor 1201 whose gate 1202 may vary between ground voltage 501 (switch off) and a positive voltage (switch on). The turn-off of transistors 1200.1 and 1200.2 may be passively done by resistor 1203 (e.g. 100 kΩ).

Figure 13:
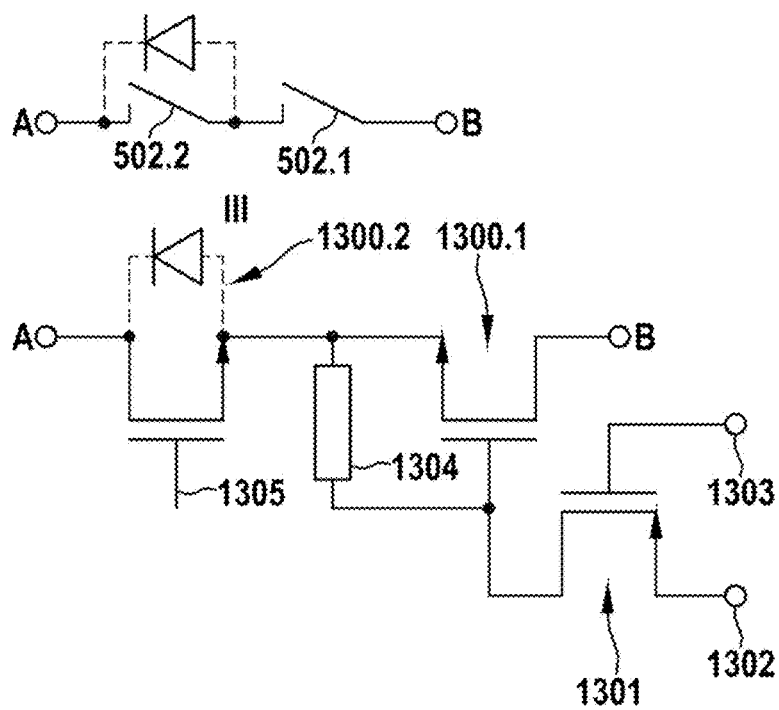
FIG. 13 shows a version wherein analog switches are implemented using back-to-back NMOS transistors.

Analog switches 502.1 and 502.2 (and the equivalents not drawn for the other contacts) may be implemented using back-to-back NMOS transistors 1300.1 and 1300.2 as shown in FIG. 13, with transistor 1300.1 enabled by PMOS transistor 1301 with its source 1302 connected to a positive voltage and its gate 1303 varying between the positive voltage (switch off) and ground voltage 501 (switch on). The turn-off of transistor 1300.1 may be passively done by resistor 1304 (e.g. 100 kΩ). The gate 1305 of transistor 1300.2 is driven by the control logic 50 in the IPG 106 to implement the VNS therapy.

Figure 14:
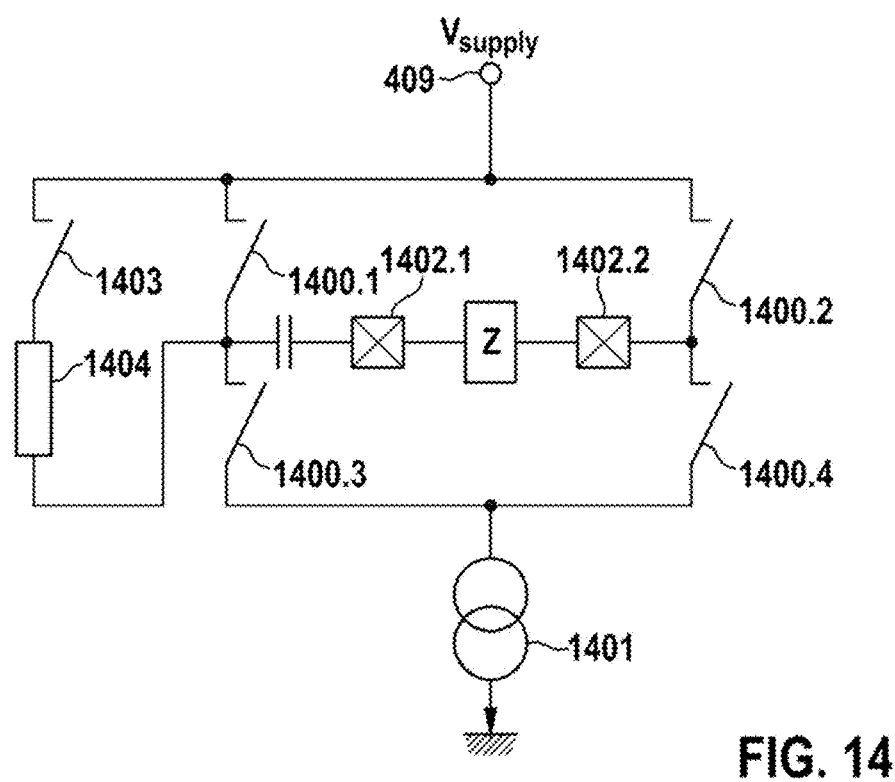
FIG. 14 shows an alternative version wherein the therapy train is delivered by an H-bridge circuit.

In an alternative version, the therapy train is delivered by an H-bridge circuit as schematically shown in FIG. 14 Analog switches 1400.1 and 1400.4 allow the stimulating current 1401 to flow from electrode 1402.1 to 1402.2, whereas analog switches 1400.2 and 1400.3 allow current 1401 to flow in the opposite direction. The stimulation current 1401 can be reprogrammed on the fly by the control logic 50 in the IPG 106 to implement arbitrary shapes.

Figure 15:
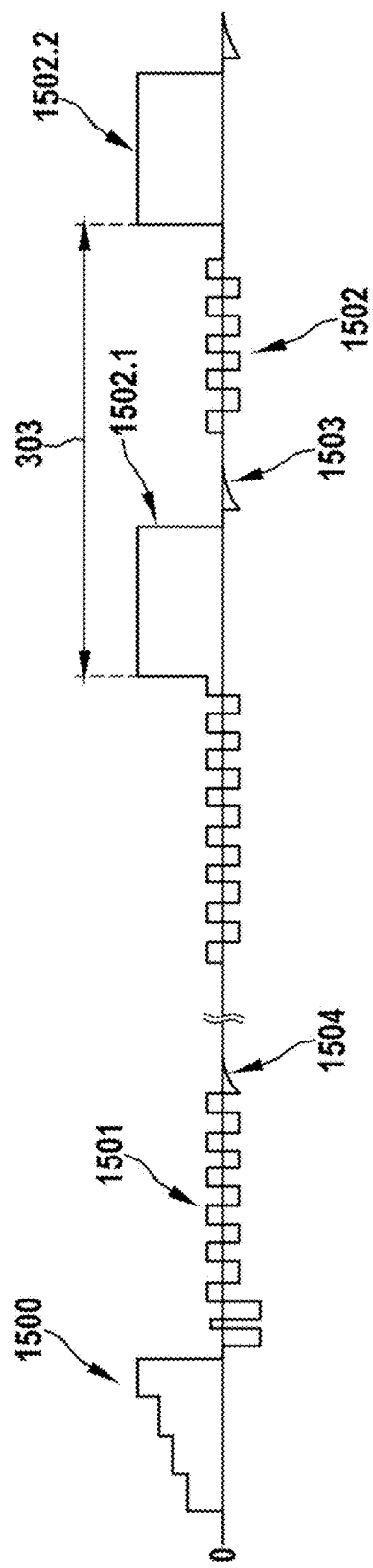
FIG. 15 shows an exemplary therapy train (not to scale) with a selective-arrest phase.

FIG. 15 shows an exemplary therapy train (not to scale) with a selective-arrest phase 1500 implemented using sub-threshold pre-depolarization pulses, with the selective-arrest phase 1500 transitioning into a charge-balanced rectangular waveform 1501 of sufficient amplitude to keep the largest diameter fibers from conducting. Therapy pulses can be square pulses 1502, which are created by unbalancing the waveform 1501 and increasing its amplitude, with associated passive charge-balancing 1503. The passive charge-balancing phase 1503, as well as passive charge-balancing phases 1504 when waveforms 1501 are temporarily stopped, may be implemented with the analog switch 1403 and the current-limiting resistor 1404 of FIG. 14.

Figure 16:
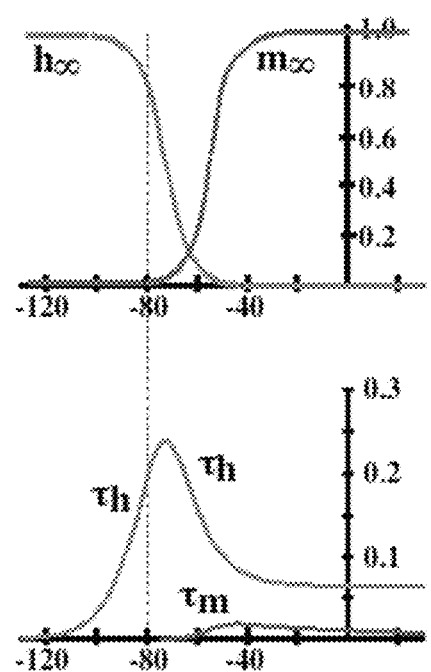
FIG. 16 shows a common model of the sodium channel gate response at a range of transmembrane potentials.

FIG. 16 shows the voltage and time response of a well-known model of the sodium channel, which is primarily responsible for depolarization in neural excitation. At low transmembrane potentials, for example −120 mV, the m-gate responsible for allowing sodium ion transport has a probability of being open near 0, indicating that the channel is closed. The h-gate, responsible for inactivation of the sodium ion channel, has a probability of being open near one. Both h and m gates must be open to allow sodium ions into the neuron, facilitating an action potential. The lower graph shows that the time constant of h-gate transitions is substantially greater than that of m-gate transitions at all transmembrane potentials and especially at the transmembrane resting potential. Thus, the invention preferably allows for a gate transition from h-open to h-closed while disallowing the m-gates in an axon to open with sufficient probability to generate an action potential. This is facilitated by the transition from anodic hyperpolarization stimulation to kHz AC stimulation.

Advantages achieved by the invention include:

1) an implantable device utilizing a cervical multi-contact nerve cuff electrode capable of selectively stimulating the vagus nerve for cardiovascular effects via a multi-phase waveform;

2) the stimulation method maximizes the ratio of heart rate reduction to side effects caused by unwanted stimulation of the larynx and pharynx; and 3) the stimulation method limits the recruitment of large-diameter fibers, associated with side effects, to the first pulse of a therapy pulse.

The versions of the invention discussed above are exemplary, and the invention can assume different forms. In particular, the device can be implanted on either the right or left vagus nerve. Features of the invention can be adapted to different kinds of implantable pulse generators and nerve stimulators by following the concepts described herein. The invention is not intended to be limited to the exemplary versions described above, but rather is intended to be limited only by the claims set out below. Thus, the invention encompasses all different versions that fall literally or equivalently within the scope of these claims.

What is claimed is:

1. An implantable pulse generator (106) connected or connectable to a stimulation lead (100) having stimulation electrodes (102, 104) for delivery of stimulation pulses, the implantable pulse generator (106) including:
   a. a stimulation unit (36, 38, 40, 42, 44, 46, 48) configured to generate electric stimulation pulses for nerve stimulation,
   b. a control unit (50) configured to trigger delivery of generated electric stimulation pulses via selected stimulation electrodes (102, 104), wherein the electric stimulation pulses form a pulse train including:
      i) an initial selective-arrest phase configured to arrest action potentials of large-diameter nerve fibers in the vicinity of the selected stimulation electrodes, the selective-arrest phase being effected by rectification of alternating current (AC) generated by the stimulation unit (36, 38, 40, 42, 44, 46, 48),
      ii) followed by a charge-balanced phase wherein charge-balanced alternating current is applied between the same or other selected stimulation electrodes,
      iii) and where such charge-balanced alternating current is briefly unbalanced to deliver a nerve stimulation therapy pulse, with charge-balanced alternating current again being applied following the therapy pulse.

2. The implantable pulse generator (106) of claim 1 wherein the stimulation electrodes (102, 104) include:
   a. a ring electrode (104), and
   b. a contact (102) defining an electrode with a smaller contact surface than the ring electrode (104).

3. The implantable pulse generator (106) of claim 2 wherein the stimulation electrodes (102, 104) include:
   a. a pair of ring electrodes (104.1, 104.2) axially spaced from each other, and
   b. at least two contacts (102) situated between the ring electrodes (104.1, 104.2).

4. The implantable pulse generator (106) of claim 3 wherein the control unit (50) is configured to trigger bipolar stimulation between:
   a. a pair of the contacts (102), or
   b. a contact (102) and at least one of the ring electrodes (104).

5. The implantable pulse generator (106) of claim 1 wherein the stimulation lead (100) includes a nerve cuff (100) having the stimulation electrodes (102, 104) thereon.

6. The implantable pulse generator (106) of claim 1 wherein the control unit (50) is configured to trigger the pulse train such that the pulse train is time duty-cycled.

7. The implantable pulse generator (106) of claim 1 wherein the control unit (50) is further configured to trigger delivery of a pulse train effecting a passive charge-balancing phase, wherein selected stimulation electrodes (102, 104) are short-circuited during the passive charge-balancing phase.

8. The implantable pulse generator (106) of claim 7 wherein the passive charge-balancing phase includes successive stages, with each stage using a different combination of stimulation electrodes (102, 104) than any immediately prior stage.

9. The implantable pulse generator (106) of claim 1 wherein the control unit (50) is configured to terminate nerve stimulation therapy by interrupting the pulse train.

10. The implantable pulse generator (106) of claim 9 wherein the control unit (50) is further configured to trigger delivery of a pulse train effecting a passive charge-balancing phase immediately after termination of nerve stimulation therapy, wherein selected stimulation electrodes (102, 104) are short-circuited during the passive charge-balancing phase.

11. The implantable pulse generator (106) of claim 1 wherein the stimulation unit (36, 38, 40, 42, 44) includes or is connected to a switched amplifier for generating the alternating current (AC).

12. The implantable pulse generator (106) of claim 11 wherein the switched amplifier is a low-Q Class-E amplifier configured to generate alternating current (AC) with a main frequency from hundreds of Hz to tens of kHz.

13. The implantable pulse generator (106) of claim 1 wherein the implantable pulse generator (106) is configured to effect the selective-arrest phase by rectification of the alternating current (AC) with an envelope approximating a quasi-trapezoidal (QT) pulse.

14. The implantable pulse generator (106) of claim 1 wherein the implantable pulse generator (106) is configured to provide pre-depolarization sub-threshold pulses during the selective-arrest phase.

15. The implantable pulse generator of claim 1 wherein:
  a. the selective-arrest phase of the pulse train is configured to arrest action potentials of large-diameter laryngeal and/or pharyngeal nerve fibers in the vicinity of the selected stimulation electrodes, and
  b. the charge-balanced alternating current of the charge-balanced phase is configured to promote blocking of conduction by large-diameter laryngeal and/or pharyngeal nerve fibers.

16. The implantable pulse generator of claim 1 wherein the nerve stimulation therapy pulse is:
  a. unbalanced, and
  b. configured to stimulate parasympathetic activity in smaller-diameter cardiac nerve fibers.

17. An implantable pulse generator configured to deliver electric nerve stimulation pulses to selected electrodes within a set of stimulation electrodes, wherein the electric nerve stimulation pulses define a pulse train including:
  a. an initial selective-arrest phase including one or more pulses configured to arrest action potentials of large-diameter nerve fibers nearby the stimulation electrodes,
  b. a subsequent charge-balanced phase wherein charge-balanced alternating current pulses are applied between the same or other selected stimulation electrodes,
  c. wherein:
    i) the pulses of the selective-arrest phase are generated by rectifying the charge-balanced alternating current pulses of the charge-balanced phase, and
    ii the charge-balanced alternating current pulses are interrupted by a nerve stimulation therapy phase including one or more unbalanced nerve stimulation therapy pulses, with charge-balanced alternating current pulses following the therapy pulses.

18. The implantable pulse generator of claim 17 wherein the pulses of the selective-arrest phase define a quasi-trapezoidal envelope bounded by:
  a. an at least substantially square leading edge defined by a sudden current increase, followed by
  b. a plateau defined by at least substantially constant current, followed by
  c. an at least substantially exponential trailing phase defined by decreasing current, with the rate of decrease diminishing over time.

19. The implantable pulse generator of claim 17 wherein the pulse train of the electric nerve stimulation pulses further include a passive charge-balancing phase wherein at least some of the stimulation electrodes are short-circuited.

20. The implantable pulse generator of claim 17 wherein:
  a. the selective-arrest phase is configured to arrest action potentials of large-diameter laryngeal and/or pharyngeal nerve fibers in the vicinity of the selected stimulation electrodes,
  b. the charge-balanced phase is configured to promote blocking of conduction by large-diameter laryngeal and/or pharyngeal nerve fibers, and
  c. the nerve stimulation therapy phase is configured to stimulate parasympathetic activity in smaller-diameter cardiac nerve fibers.

21. The implantable pulse generator of claim 17 wherein the nerve stimulation therapy pulses are:
  a. unbalanced, and
  b. configured to stimulate parasympathetic activity in smaller-diameter cardiac nerve fibers.

22. A method of delivering electric nerve stimulation pulses from an implantable pulse generator to selected electrodes within a set of stimulation electrodes, the method including delivering the electric nerve stimulation pulses as a pulse train including:
  a. an initial selective-arrest phase including one or more pulses configured to arrest action potentials of large-diameter nerve fibers nearby the stimulation electrodes, the selective-arrest phase being effected by rectification of alternating current (AC) pulses;
  b. a subsequent charge-balanced phase wherein charge-balanced alternating current pulses are applied between the same or other selected stimulation electrodes, the alternating current pulses being configured to promote blocking of conduction by the large-diameter nerve fibers,
  c. wherein the charge-balanced alternating current pulses are interrupted by a nerve stimulation therapy phase including one or more unbalanced nerve stimulation therapy pulses configured to stimulate parasympathetic activity, with the charge-balanced alternating current pulses again being applied following the nerve stimulation therapy phase.

23. The method of claim 22 wherein:
  a. the selective-arrest phase is configured to arrest action potentials of large-diameter laryngeal and/or pharyngeal nerve fibers in the vicinity of the selected stimulation electrodes,
  b. the charge-balanced phase is configured to promote blocking of conduction by large-diameter laryngeal and/or pharyngeal nerve fibers, and
  c. the nerve stimulation therapy phase is configured to stimulate parasympathetic activity in smaller-diameter cardiac nerve fibers.

24. The method of claim 22 wherein the nerve stimulation therapy pulses are:
  a. unbalanced, and
  b. configured to stimulate parasympathetic activity in smaller-diameter cardiac nerve fibers.

* * * * *